US 7,314,374 B2

(12) United States Patent
Augthun et al.

(10) Patent No.: US 7,314,374 B2
(45) Date of Patent: Jan. 1, 2008

(54) DOWEL-SHAPED ELEMENT FOR DETERMINING SPATIAL POSITION, ESPECIALLY THAT OF AN IMPLANT

(75) Inventors: Michael Augthun, Aachen (DE); Manfred Peters, Wolfenbüttel (DE); Klaus Haselhuhn, Aachen (DE); Hubertus Spiekermann, Haan (DE)

(73) Assignee: Heraeus Kulzer GmbH & Co., KG, Hanau (DE)

( * ) Notice: Subject to any disclaimer, the term of this patent is extended or adjusted under 35 U.S.C. 154(b) by 0 days.

(21) Appl. No.: 10/258,246

(22) PCT Filed: Apr. 5, 2001

(86) PCT No.: PCT/EP01/03859

§ 371 (c)(1),
(2), (4) Date: Feb. 14, 2003

(87) PCT Pub. No.: WO01/80767

PCT Pub. Date: Nov. 1, 2001

(65) Prior Publication Data

US 2003/0170588 A1    Sep. 11, 2003

(30) Foreign Application Priority Data

Apr. 19, 2000   (DE) ................................. 100 19 331

(51) Int. Cl.
*A61C 19/04* (2006.01)
*A61C 8/00* (2006.01)

(52) U.S. Cl. ........................................ 433/173; 433/72

(58) Field of Classification Search ................ 433/173, 433/175, 176, 72
See application file for complete search history.

(56) References Cited

U.S. PATENT DOCUMENTS 4,293,302 A * 10/1981 Hassler et al. .............. 433/173

(Continued)

FOREIGN PATENT DOCUMENTS

DE            7112381           3/1971

(Continued)

OTHER PUBLICATIONS

Abstract of DE 4326841 from EPO website database.

*Primary Examiner*—Cris L. Rodriguez
*Assistant Examiner*—Candice C. Stokes
(74) *Attorney, Agent, or Firm*—Norris, McLaughlin & Marcus PA

(57) ABSTRACT

A post-shaped element for determining the alignment of an implant (10), or the opening cross-section of an artificial indentation located in a tooth or in the stroma of a human or animal body, relative to the surrounding tissue structures, can be introduced with a receiving section (28, 26A) into an adapted receiving recess (10) in the implant (1) or the artificial indentation, and be affixed therein and removed again. In a connecting position the post-shaped element protrudes with a cantilever section (26K) beyond the opening cross-section of the receiving recess (10) or the artificial indentation. In order to be able determine the correct position of the post-shaped element in relation to the implant (1) in a simple and reliable manner without X-ray images, it is suggested that the post-shaped element contain a through-hole extending in the direction of its longitudinal axis, through which a rod device (32) can be guided, which with a distal stop surface (36) can be brought into contact with a stop surface (37) on the base of the receiving recess (10) of the implant (1).

12 Claims, 5 Drawing Sheets

U.S. PATENT DOCUMENTS

Figure 8:
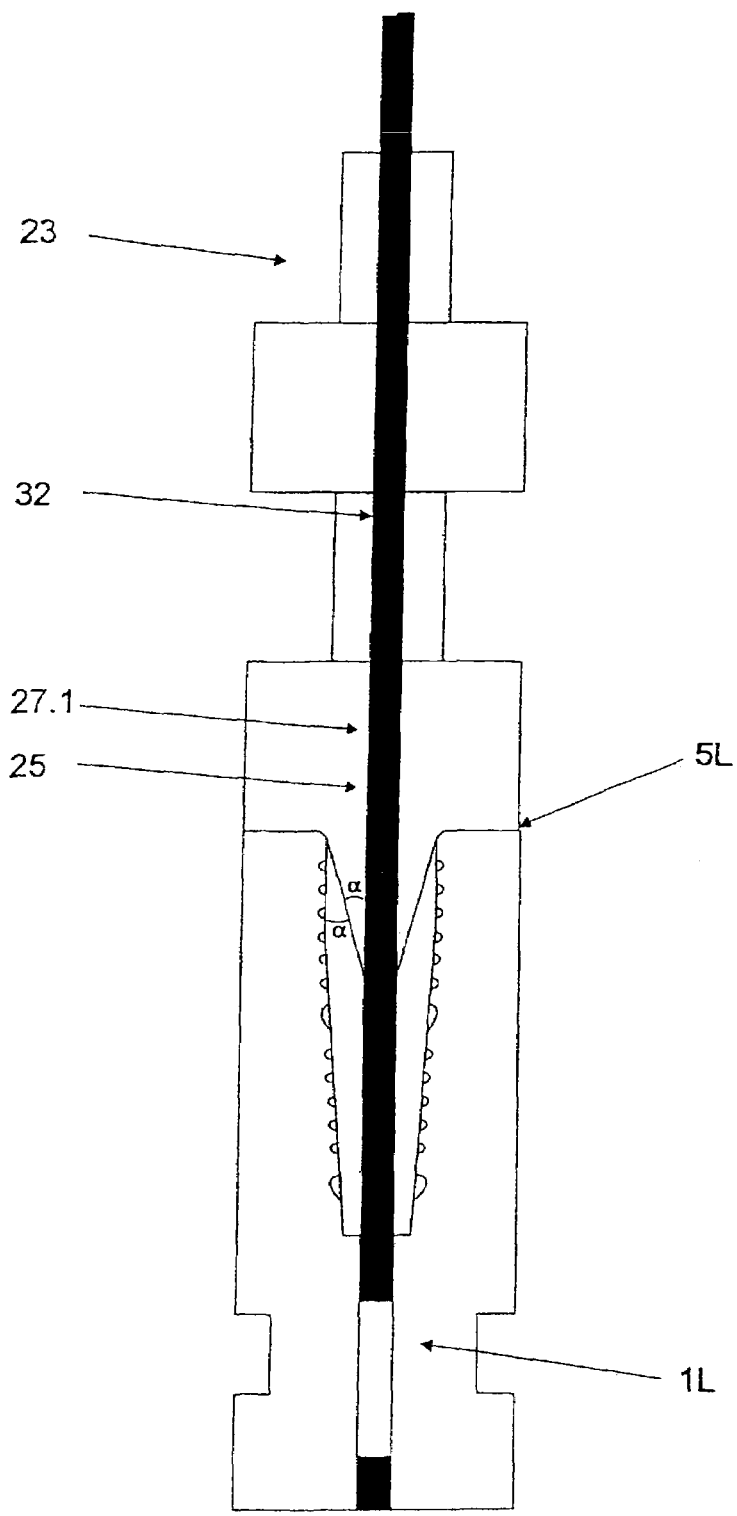

| | | | |
|---|---|---|---|
| 4,708,654 A | 11/1987 | Branemark | 433/213 |
| 5,246,370 A | 9/1993 | Coatoam | 433/173 |
| 5,281,140 A | 1/1994 | Niznick | 433/172 |
| 5,538,424 A * | 7/1996 | Gelb | 433/72 |
| 5,782,918 A | 7/1998 | Klardie et al. | 623/16 |
| 6,206,696 B1 | 3/2001 | Day | |
| 6,565,357 B1 * | 5/2003 | Lazzara et al. | 433/173 |
| 6,644,969 B2 | 11/2003 | Kumar | |

FOREIGN PATENT DOCUMENTS

| | | |
|---|---|---|
| DE | G 92 00264.1 | 4/1992 |
| DE | 43 26 841 A1 | 2/1995 |
| DE | 100 19 338 A1 | 11/2001 |
| DE | 103 33 013 A1 | 2/2005 |
| GB | 2 211 416 A | 7/1989 |
| WO | WO 97/28756 | 8/1997 |

* cited by examiner

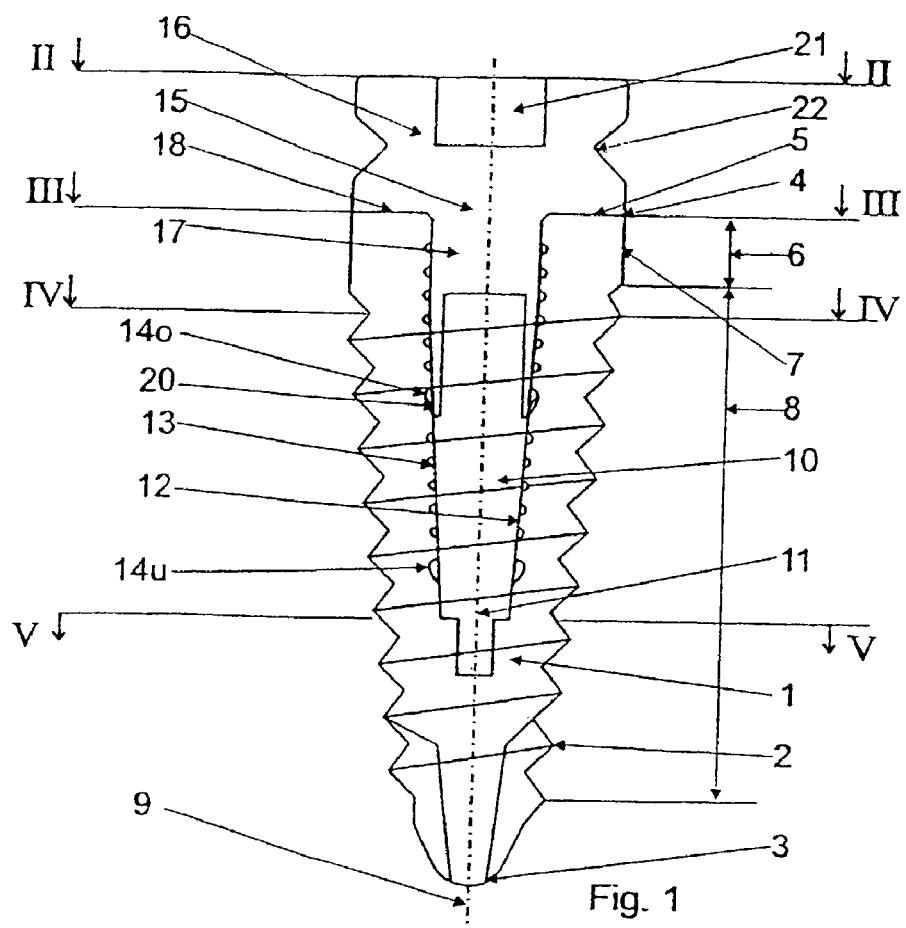
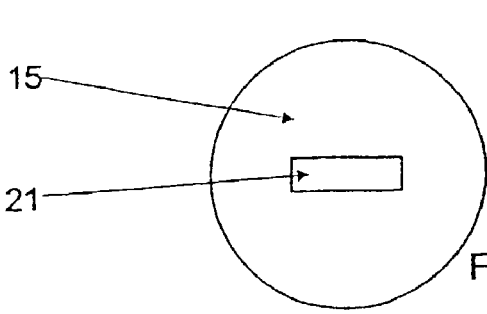
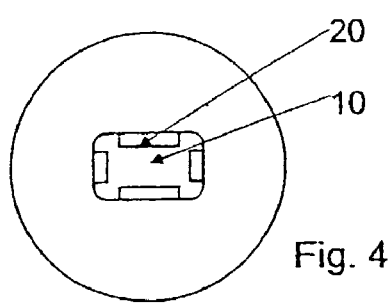
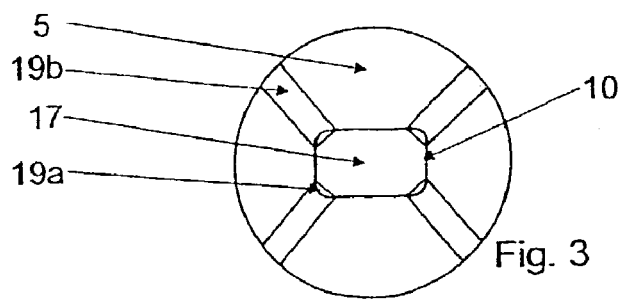
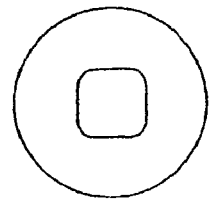

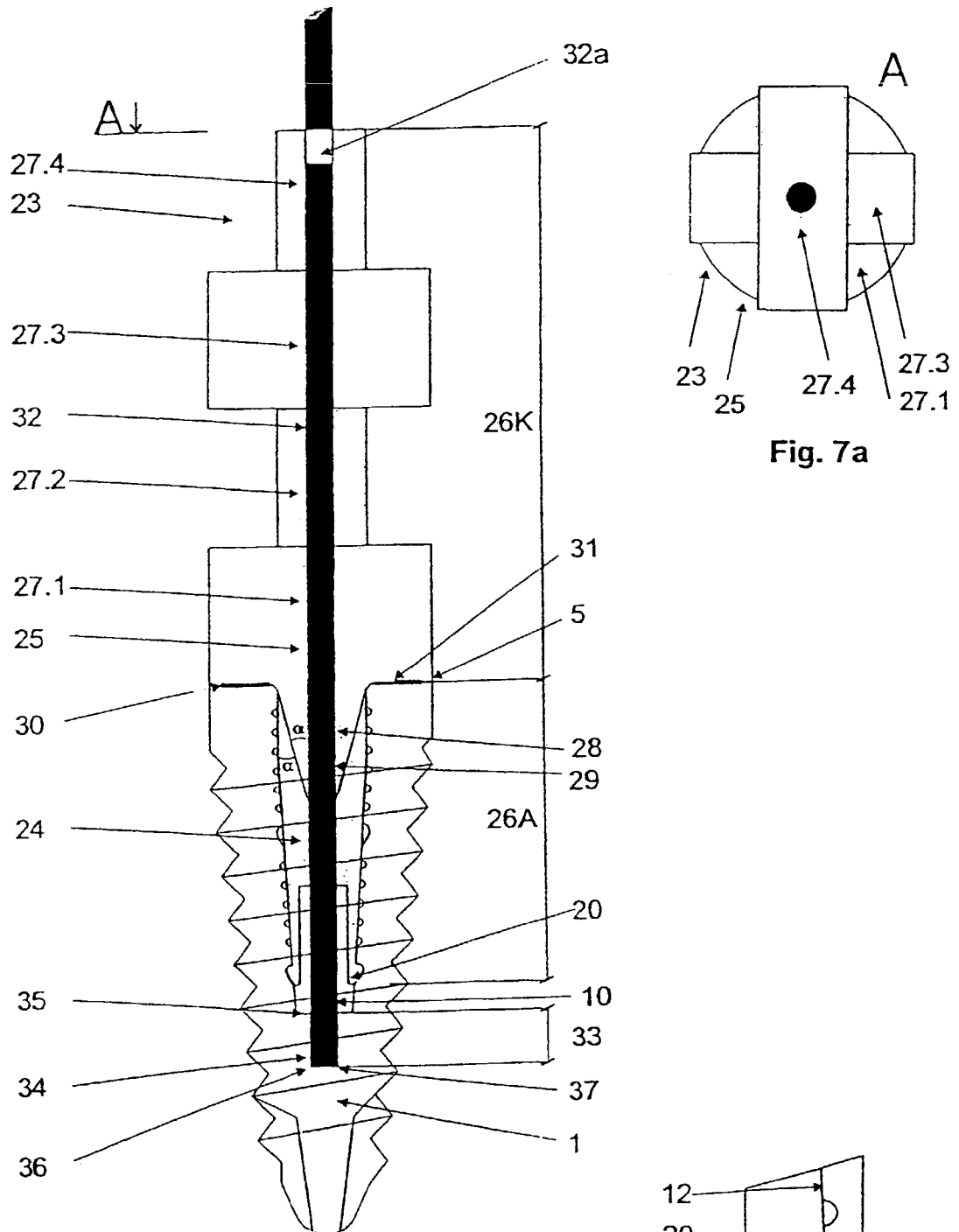
Fig. 7
Fig. 7a
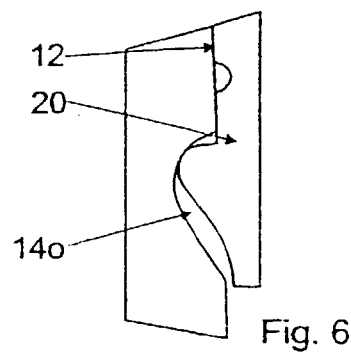
Fig. 6

DOWEL-SHAPED ELEMENT FOR DETERMINING SPATIAL POSITION, ESPECIALLY THAT OF AN IMPLANT

This application is a 371 of PCT/EP01/03859, filed on Apr. 5, 2001.

The invention relates to a post-shaped element for determining the spatial position of an implant, or the opening cross-section of an artificial indentation located in a tooth or in the stroma of a human or animal body, relative to the surrounding tissue structures, wherein the post-shaped element with receiving recess can be introduced into an adapted receiving recess in the implant or in the artificial indentation, be fixed therein and removed therefrom again and in the connecting position protrudes with a cantilever section protrudes beyond the opening cross-section of the receiving recess or the artificial indentation.

In dentistry such post-shaped elements are described as so-called impression posts, which for example, make it possible to determine the position and alignment of a dental implant previously introduced into a jawbone. For this purpose the post-shaped element is inserted with the bottom portion designed as a receiving section into a bore in the implant functioning as a receiving recess and fixated therein for example with the help of an axially connecting screw in a threaded bore on the inside of the implant. The cantilever section protruding in the implant beyond the opening cross-section in the connecting position of the post-shaped element is typically equipped with multiple retention features in order to establish as close a positive lock between the cantilever section and a curable impression mass as possible.

With the aid of an impression tray the space around the impression post as well as the neighboring teeth is filled in with an impression mass that is initially moldable, making a kind of negative impression to be created of the teeth and the impression post.

In an area that is allocated to the proximal end of the cantilever section of the impression post, the impression tray exhibits a recess in order to be able to twist the fixating screw out after the impression mass has been able to cure. After the fixation of the post-shaped element in the implant has been eliminated again, the post-shaped element, which is positively embedded in the impression mass, can be removed together with the mass from the jaw.

One disadvantage with the familiar impression posts is that their correct position in relation to the implant cannot be established without difficulty during the insertion and before the impression processes. It is quite possible for adjacent tissue to have become inserted between the contact surfaces of the impression post and the implant, which rest against each other in the case of correct positioning, so that the impression post and the implant cannot find the correct position in relation to one another. In this case, the impression would maintain an incorrect position of the impression post, allowing a conclusion of an incorrect position of the implant.

In order to avoid this uncertainty, the correct position of the impression post is checked with the help of an X-ray image after fixation of the impression post in the implant and before the impression process. This X-ray image leads to increased time requirements during installation and thus costs for such an implant system are higher; additionally it exposes the patient to radiation, which based on existing findings should be minimized to the extent possible.

The invention is therefore based upon the task of suggesting a post-shaped element for determining the spatial position, especially of an implant, with which the correct position of the post-shaped element in relation to the implant can be established easily and reliably and without the aid of X-ray images before the impression process.

Proceeding from a post-shaped element of the above-described kind, this task is resolved pursuant to the invention in that the post-shaped element contains a through-hole extending in the direction of its longitudinal axis, wherein a rod device can be guided through said through-hole and be brought into contact with a distal stop surface on the base of the receiving recess of the implant.

By inserting the rod device on the adapted through-hole, one can detect easily whether the post-shaped element is in the correct position in relation to the implant. The rod device, which is preferably designed longer than the through-hole, is inserted into the through-hole until it comes into contact on its distal stop surface with a stop surface on the base of the receiving recess of the implant. Since the length of the through-hole through the post-shaped element is known, one can read depending on the length of the rod device that is received by the through-hole whether the post-shaped element is in the correct position. If the rod device can be inserted deeper into the through-hole than should be the case with the correct position of the post-shaped element, then this allows the conclusion that the post-shaped element due to some circumstances is located still away from the implant, allowing for example the conclusion of trapped tissue between the contact surfaces of the post-shaped element and the implant.

In the post-shaped element pursuant to the invention it is thus possible to control its correct position solely with the help of a visual and/or mechanical aid. The X-ray images of the position of the post-shaped element can be foregone completely, leading to a reduction in costs and in the patient's exposure to radiation.

Pursuant to one embodiment of the invention, it is suggested that the through-hole and the receiving recess run in a coaxial manner to each other.

Additionally it is beneficial if the rod device can be inserted with a distal end section into an opening in the base of the receiving recess that has been adapted in its cross-section. In this case the rod device conveys the "post-shaped element-implant" composite stability that makes it possible to forego possibly any other type of fixation during the impression process.

Insertion of the post-shaped element is facilitated when the opening expands slightly in the area of its entry cross-section and/or the rod-shaped element is slightly tapered in its diameter in its distal end section.

The reading of the rod device's position is simplified by designing the proximal end face of the post-shaped element such that it runs at a right angle to the longitudinal axis of the rod device.

Additionally it is beneficial that the rod device on its outer surface area is equipped with a marking, which in the case of a correct position of the post-shaped element in relation to the implant and upon contact of the stop surfaces of the post-shaped element with those of the implant is just barely completely inserted in the through-hole or is located just above the opening cross-section of the through-hole.

A particularly beneficial application of the post-shaped element pursuant to the invention consists of designing it as an impression post for determining the alignment of a dental implant.

The post-shaped element pursuant to the invention is explained in more detail in the following with the help of one example, which is shown in the drawing.

It shows:

FIG. 1 Implant with a clipped-on cap in a longitudinal sectional view;

FIG. 2 Top view onto the cap;

FIG. 3 Top view onto the implant upon removal of the cap;

FIG. 4 Cross-sectional view along line IV-IV through the implant pursuant to FIG. 1;

FIG. 5 Cross-sectional view along line V-V through the implant pursuant to FIG. 1;

FIG. 6 an enlarged section of the engagement area of a clip element;

FIG. 7 Implant with a clipped-on two-piece impression post in a longitudinal cross-sectional view;

FIG. 7a Top view onto the upper portion of the impression post pursuant to FIG. 7;

FIG. 8 As in FIG. 7, however of a lab implant.

Figure 9:
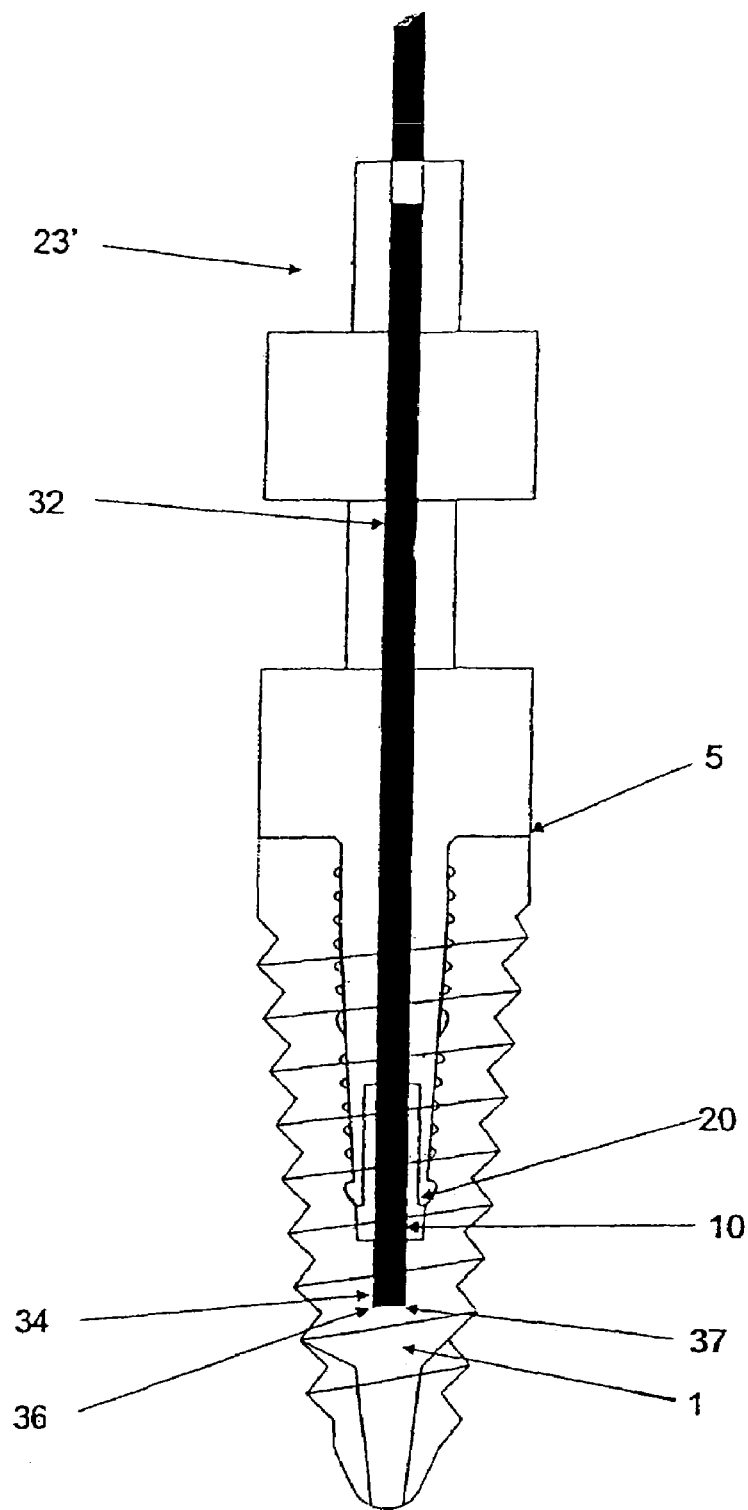

FIG. 9 As in FIG. 7, however of a single-piece impression post, and

Figure 10:
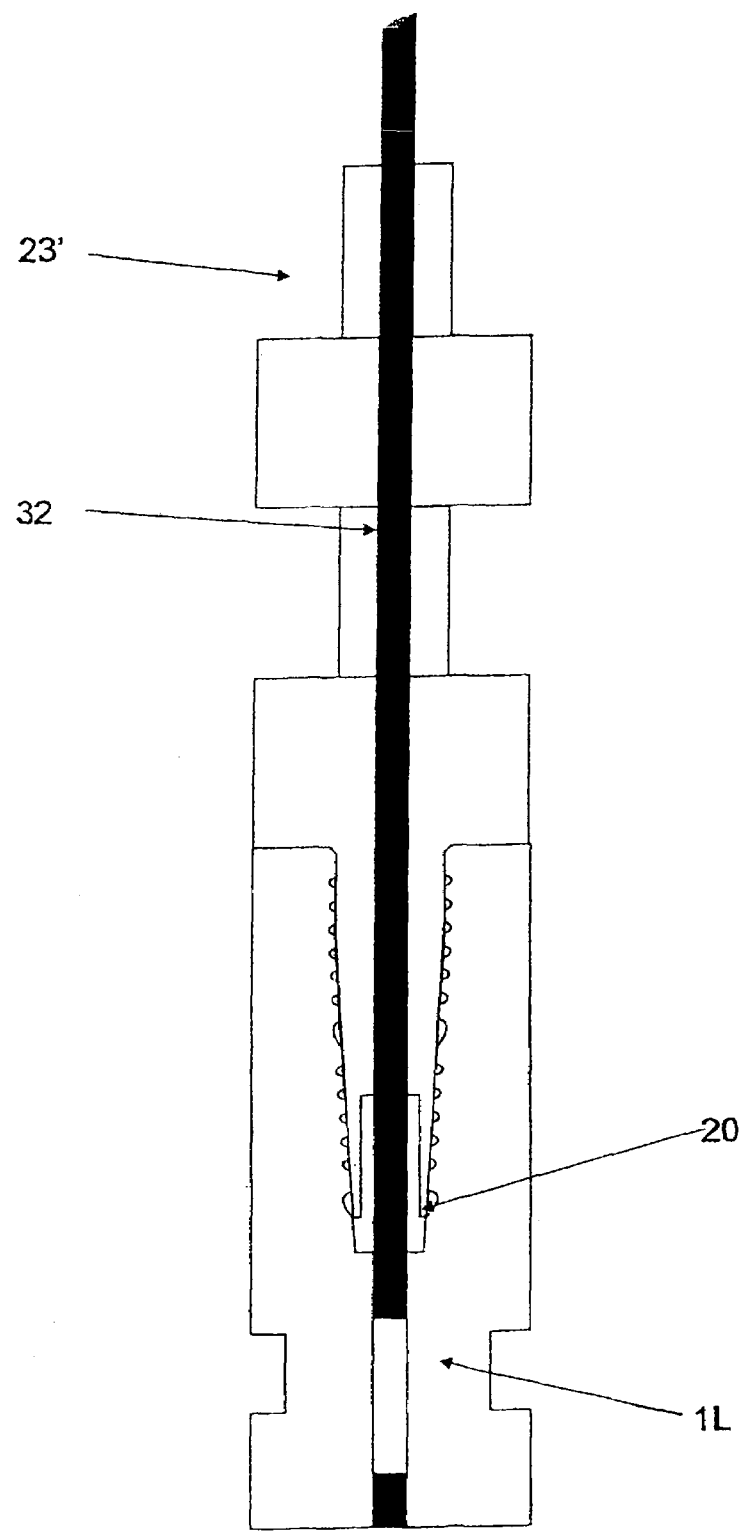

FIG. 10 As in FIG. 9, however of a lab implant.

FIGS. 1 through 5 reveal an implant 1 consisting of titanium, which has a roughly conical base shape and on its outer surface area contains an outer thread 2. The implant 1 contains a rounded-off distal end 3 and a proximal end 4, which is formed by a largely circular end face 5. In a section 6 following the end face 5, the implant 1 exhibits cylindrical shape with a high-polished surface area 7. In a threaded area 8 that follows, the implant 1 has a conical design. Starting from the end face 5, parallel to the longitudinal axis 9 of the implant, a receiving recess 10 extends, which runs across the entire length of the section 6 as well as a portion of the length of the threaded section 8.

As FIG. 3 shows, the cross-section of the receiving recess 10 takes on the shape of a rounded-off rectangle in the area of the section 6. Starting with the threaded area 8, the cross-section of the receiving recess 10 tapers continuously so that on the base 11 of the receiving recess 10 the cross-section has the shape of a rounded-off square (see FIG. 5). The transition from the rounded-off rectangular to the rounded-off square cross-sectional shape occurs continuously and smoothly.

As particularly FIG. 1 shows, the wall 12 of the receiving recess 10 contains a plurality of ring grooves 13, which are aligned vertical to the longitudinal axis 9. Furthermore the wall 12 is equipped with an upper and a lower ring groove 14o and 14u, the function of which is explained below.

The implant 1 depicted in FIG. 1 is inserted in a cap 15, consisting of a roughly cylindrical head portion 16 and a coaxially thereto aligned connecting broach 17, which extends in the receiving recess 10. A contact surface 18 of the head portion 16 rests positively on the end face 5 of the implant 1.

As FIG. 3 reveals, the connecting broach 17 has in its upper section a roughly rectangular cross-section, wherein the corner areas are broken in such a way that in the rounded-off areas of the cross-section of the receiving recess 10 between the connecting broach 17 and the wall 12 of the receiving recess 10 four ventilation ducts 19a are formed. Air displaced when inserting the connecting broach 17 in the receiving recess 10 can thus flow out upward without causing a pressure build-up that would impair the assembly process, wherein the air can escape to the outside through four radially outward extending ventilation grooves 19b, which are incorporated in the end face 5 of the implant and communicate with the ventilation ducts 19a.

In the installed state of the cap 15, the outer surface areas of the connecting broach 17 and the wall 12 of the receiving recess 10 as well as the end face 5 and the contact surface 18 rest positively against each other.

Since the cap 15 remains on the implant 1 only temporarily after implantation, it is connected with the implant 1 only through four clip elements 20, which engage with the clip groove 14o. Instead of the engagement of the clip devices 20 in the upper clip groove 14o shown in FIG. 1, engagement in the lower clip groove 14u is also possible with an appropriately extended connecting broach 17.

The cap 15 is inserted into the implant 1 already by the implant manufacturer and upon preparation of an appropriate bore in the bone serves the purpose of screwing the implant 1 in with the help of a screwdriver, which engages with the slot 21 shown in FIG. 2. Due to the roughly rectangular cross-section of the connecting broach 17 and the adapted receiving recess 10, the introduction of moments of torsion into the implant 1 is possible via the cap 15. Upon implantation, the cap 15 remains on the implant 1 in order to protect also the receiving recess 10 from outside contamination.

Approximately 3 to 6 months after insertion of the implant 1 in the jaw bone, the healing process is completed far enough to be able to open up the mucous membrane covering the cap 15 in a second surgery. The cap 15 is removed, which is accomplished by reaching into a V-shaped ring groove 22 in the head portion 16 with the help of a tool in the shape of tongs and removing the entire cap 15 upward from the implant with a slight jerk in the axial direction. Into the receiving recess 10 of the implant 1 now a connecting broach 17 of a gingiva former is inserted, which is not shown in the figures. The fastening principle of the gingiva former is the same as with the cap.

In order to be able to adapt a replacement tooth, which is to be anchored in the implant 1, outside the mouth area of the patient to a model of the jaw, an impression of the teeth is prepared. For this purpose, a post-shaped element, which is shown in FIG. 7, in the shape of an impression post 23 is inserted into the receiving recess 10 of the implant. The impression post 23 consists of a bottom portion 24, which can be fixated in the receiving recess with four clip devices 20, and a top portion 25, which can be torsional-resistantly inserted into the bottom portion 24. The top portion 25 protrudes with a cantilever section 26K beyond the opening cross-section of the receiving recess 10 and is composed of four cuboid devices 27.1 through 27.4. The lowest device 27.1 exhibits a conical end section 28 with an elliptic cross-section, which engages with an indentation 29 of complementary design in the bottom portion 24 of the impression post 23. The bottom portion 24 ends with its upper edge flush with the end face 5 of the implant 1. The indentation 29 extends directly from the level of the end face 5 and has an opening cross-section that is only slightly smaller than the opening cross-section of the receiving recess 10 in the implant 1 itself.

As the top view onto the top portion 25 of the impression post 23 pursuant to FIG. 7a reveals, the cuboid devices 27.1 through 27.4, which have a rectangular outline, are turned towards each other alternately by 90°, i.e. in a cross-shaped stacked manner.

The lowest device 27.1 of the top portion 25 of the impression post 23 rests with its circular contact surface 30 against the end face 5 of the implant 1, wherein for the purpose of secure fixation of the impression post 23 to the implant 1 on the contact surface 30 after the preparation of the impression post 23, which is done in an injection molding process, a thin peripheral adhesive ring 31 is applied, which can be removed with a slight jerky movement again from the end face 5 of the implant 1 after the impression has been taken.

Proceeding from the connecting position shown in FIG. 7, the top portion 25 of the impression post 23 is surrounded by a viscous and curable impression mass. After the curing process, the impression post 23 cannot be removed any longer from the impression mass without destroying the positive connection. Rather the impression tray, which contains the impression mass, is removed together with the impression post 23, wherein the adhesive connection established by the adhesive ring 31 is removed by applying a slight jerky movement. Due to the conical connection with elliptic cross-section between the top portion 25 and the bottom portion 24 of the impression post 23, the top portion 25 can be removed in a linear fashion from the implant 1 and/or the initially remaining bottom portion 24 in various directions. The limits of the possible directions are defined by the surface area of the cone of the end section 28 and/or the complementary indentation 29 when said surface area is extended upward beyond the end face 5 of the implant 1. Due to the special connection of the bottom portion 24 with the top portion 25, the latter can be removed from the mouth area without tension and without applying force onto the impression mass even if the longitudinal axis of the implant 1 exhibits a quite considerable slanted position in relation to the neighboring teeth.

The impression post 23 depicted in FIG. 7 contains a continuous centrally arranged through-hole, in which an adapted rod device 32 is inserted. The rod device 32, which extends through all devices 27.1 through 27.4, penetrates with its distal end section 33 into a thereto adapted opening 34 in the base 35 of the receiving recess 10. For this purpose the rod device 32 is slightly tapered in its diameter on its distal end section, thus facilitating the insertion motion. The through-hole for the rod device 32 also extends through the end section 28 of the cylindrical device 27.1 as well as the bottom portion 24.

The rod device 32 for one allows the correct positioning of the impression post 23 to be checked, specifically when in the proximal end section of the rod device 32 a marking 32a is incorporated, which has just barely disappeared in the through-hole of the upper most device 27.4 when the contact surface 30 of the device 27.1 rests correctly against the end face 5 of the implant 1. Alternatively, the marking can also be applied such that it has not quite yet entered the through-hole in the just described state.

Another advantage of the rod device 32 is the fact that this way the impression post 23 receives greater stability. In particular it prevents that during the impression process the top portion 25 of the impression post 23 can shift relative to the bottom portion 24, for example through force that is applied by the impression mass.

It is decisive for the correct position of the rod device 32 that the distal end section 33 engages with the adapted opening 34 in the base 35 of the receiving recess 10, specifically in such a way that a distal stop surface 36 of the rod device 36 comes into contact with a stop surface 37 on the base of the opening 34.

FIG. 8 shows the top portion 25 of the impression post 23 in a lab implant 1L, the receiving recess of which is identical to that of the implant 1. The bottom most cuboid device 27.1 rests with its stop surface against the end face 51 of the lab implant. With the help of the rod device 32 a fixation of the impression post 23 in the lab implant 1L can be accomplished even without the bottom portion 24 of the impression post 23.

Additionally, the rod device 32 penetrates with its distal end 33' into a bore 34' in the base 35' of the receiving recess 10'. This ensures the correct connecting position between the lab implant 1L and the impression post 23.

FIG. 9 shows an alternative impression post 23', which has a single-piece design and can be fastened with clip devices 20 on its distal end in an appropriate ring groove in the implant 1. Due to the single-piece design of the impression post 23', it can be removed basically only in the direction of the longitudinal axis of the implant 1 or its receiving recess 10. Removal occurs with a slightly jerky motion in order to overcome the positive forces of the clip connection.

The impression post 23' as well is equipped with a central through-hole, into which the rod device 32 is inserted so far that it rests with its distal stop surface 36 on the appropriate stop surface 37 on the base of the bore 34. This way the correct seating of the impression post on the end face 5 of the implant 1 can be checked without the aid of X-ray images before preparing the impression.

FIG. 10 finally shows how the impression post 23' after the completed impression process is inserted into a lab implant 1L. Fixation here as well occurs both the help of the clip devices 20 and with the help of the rod device 32.

The invention claimed is:

1. An apparatus for determining the alignment of an implant, or the opening cross-section of an artificial indentation located in a tooth or in the stroma of a human or animal body, relative to the tissue structures surrounding it, said apparatus comprising a post-shaped element, said post-shaped element capable of receiving a rod device, wherein the post-shaped element comprises a receiving recess and can be introduced into an adapted receiving recess in the implant, be fixed therein and removed therefrom again and when fixed to the implant protrudes with a cantilever section beyond an opening cross-section of the receiving recess of the implant, wherein the post-shaped element contains a through-hole extending in the direction of its longitudinal axis, through which the rod device can be guided, which rod device with a distal stop surface can be brought into contact with a stop surface on the base of the receiving recess of the implant, wherein the rod device is not tapered over a majority of its length, and wherein the post-shaped element comprises at least one clip element, which, with a radially outward protruding projection, can positively engage with at least one indentation on an inner surface area of the receiving recess of the implant, thereby removably fixing the post-shaped element to the implant.

2. Apparatus pursuant to claim 1, wherein the through-hole and the receiving recess of the post-shaped element run in a coaxial manner to each other.

3. Apparatus pursuant to claim 1, wherein a proximal end face runs at a right angle to the longitudinal axis of the rod device.

4. Apparatus pursuant to claim 1, which is an impression post for determining the spatial position of a dental implant.

5. Apparatus pursuant to claim 1, which further comprises an implant, and the post-shaped element is introduced into an adapted receiving recess in the implant and removably fixed to the implant by means of the at least one clip positively engaging the at least one indentation on the inner surface area of the receiving recess of the implant.

6. Apparatus pursuant to claim 5, which further comprises a rod device passed through said through-hole in the post-shaped element so that a distal stop surface of the rod device is brought into contact with a stop surface on the base of the receiving recess of the implant.

7. Apparatus pursuant to claim 6, wherein the rod device with a distal end section is inserted into its cross-section adapted opening in the base of the receiving recess of the implant.

8. Apparatus pursuant to claim 7, wherein the opening is slightly expanded in the area of its entry cross-section and/or that the rod device is slightly tapered in its diameter in a distal end section.

9. Apparatus according to claim 6, wherein a portion of said rod device opposite said distal stop surface protrudes from said cantilever section of said post-shaped element.

10. Apparatus pursuant to claim 9, wherein the rod device on its outer surface is equipped with a marking, which in the case of a correct position of the post-shaped element in relation to the implant and upon contact of the stop surfaces of the rod device and the implant is just barely completely inserted in the through-hole or is just directly above the opening cross-section of the through-hole.

11. Apparatus according to claim 9, wherein the cantilever section comprises a plurality of stacked cuboid devices.

12. Apparatus according to claim 11, wherein the cuboid devices are stacked in a cross-shaped manner.

* * * * *